United States Patent [19]

de Wit

[11] Patent Number: Plant 6,269

[45] Date of Patent: Sep. 6, 1988

[54] BARBERRY PLANT

[75] Inventor: Aart de Wit, Grand Rapids, Mich.

[73] Assignee: New Plants, Perry, Ohio

[21] Appl. No.: 894,761

[22] Filed: Aug. 8, 1986

[51] Int. Cl.[4] ..... A01H 5/00

[52] U.S. Cl. ..... Plt./58

[58] Field of Search ..... Plt./58

*Primary Examiner*—Robert E. Bagwill

*Attorney, Agent, or Firm*—Watts, Hoffmann, Fisher & Heinke Co.

[57] ABSTRACT

The present invention relates to a new and distinct variety of barberry, which was discovered by me as a sport in a block of Berberis on my cultivated property at Grand Rapids, Mich. More particularly, the present invention relates to a novel cultivar of *Berberis thunbergii atropurpurea* having unusual and distinctive foliage coloration, known as "Crimson Velvet", a plant of New Plants.

1 Drawing Sheet

DESCRIPTION

1. Technical Field

The present invention relates to a new and distinct variety of Barberry plant, which was discovered by me as a seedling variant growing on my cultivated property at Grand Rapids, Mich. More particularly, the present invention relates to a novel cultivar of *Berberis thunbergii atropurpurea* having unusual and distinctive characteristics, known as "Crimson Velvet", a plant of New Plants, Perry, Ohio.

2. Background of the Plant

The *Berberis thunbergii atropurpurea* plant is of the family berberidaceae. This plant has colored foliage and exhibits purplish-red leaves especially when grown in full sun light. The plant is many branched and has a compact habit, usually 2 to 5 feet tall, Its leaves and thorns grow in tufts on the branches. The leaves are obovate in shape and ½ to 1¼ inches long. In the blooming season, pale yellow flowers about ⅓ inch wide, usually in umbellate clusters of about 2 to 5 blooms. In fall, the branches bear red berries, about ⅓ inch long, which persist through winter until new leaves grow in the spring.

DESCRIPTION OF THE PREFERRED PLANT VARIETY

Figure 1:
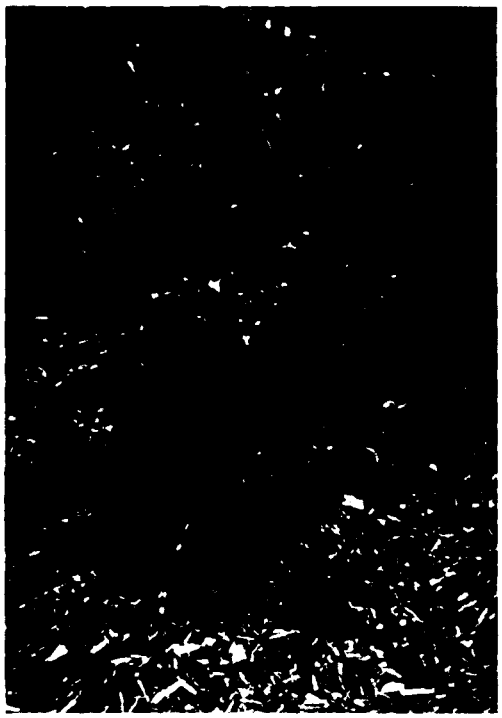
FIG. 1 illustrates my new Berberis plant in full late summer foliage.
Figure 2:
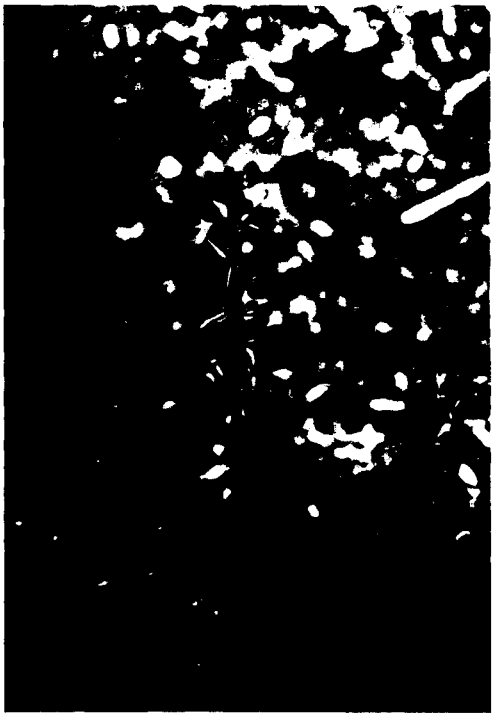
FIG. 2 illustrates a closer view of a portion of the branches of the plant illustrated in FIG. 1.
Figure 3:
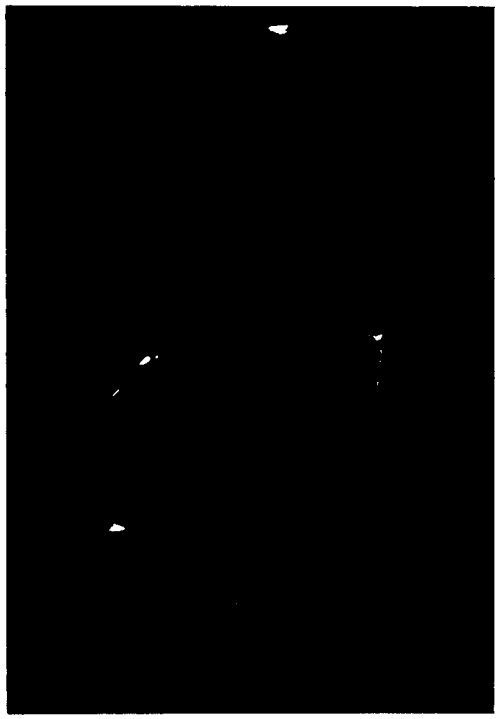
FIG. 3 illustrates a sample of leaves from the plant for purposes of clarity showing upper leaf surfaces.

In this invention, my new barberry plant has strong basal branching which develops into a fountain-like habit. As contrasted with the Berberis genus in general, my new plant exhibits lusher new growth, longer thorns and larger, more colorful leaves than the seed parent and other species of the genus grown under similar growing conditions. As contrasted with the purplish-red foliage of atropurpurea, my new plant exhibits mature leaves of smokey maroon.

The immature leaves and shoots of this plant are a bright fuchsia color which deepens to a smokey maroon upon maturity. The alternate, simple, broadly elliptic leaves are usually entire, sometimes serrate with age. The glabrous leaves are 2 inches long, of which ⅜ of an inch is the petiole. Leaf widths are about 1 to 1½ inches.

Immature twigs very in color from deep magenta at the tip to brown at the base. Leaf buds match the stem color. Older stems are cordovan brown with striations, some of which can be as wide as to give the stem a greyish appearance.

A further and important distinguishing feature of my new plant is that it has an exceptional cutting regrowth rate and takes trimming readily so that it can be maintained in the landscape as a solid hedge with dense growth at the base, as contrasted with the Berberis genus in general, which tends to form hedges with gaps toward the bases of the plants.

My new plant bears yellow flowers and red ellipsoidal berries typical of the genus. Asexually reproduction of my new barberry plant was performed at Perry, Ohio, Zone 5, by taking soft wood cuttings for summer propagation, of which more than 75% rooted and grew. The cuttings exhibited the same color and growth habit as described above. Subsequent propagations exhibited the same foliage colors. Such reproduction shows the foregoing characteristics and distinctions of my new plant take place and are established and transmitted through succeeding propagations of the barberry.

The following is a specific discription by way of a specific example of my new Barberry, the color terminology being referenced to the *Munsell Book of Color*, Neighboring Hues Edition, Baltimore Md., 1950, hereinafter referred to as Munsell.

Leaves: The established leaves are a deep smokey maroon (Munsell 7.5 P 4/2 to 2/2) having lighter maroon veins (Munsell 5 RP 4/8 to 3/8). Immature leaves are brighter maroon than the established leaves (Munsell 5 RP 5/6 to 3/6).

I claim:

1. A new and distinct cultivar of *Berberis thunbergii*, substantially as herein shown and described, characterized particularly by leaves which are of a smokey maroon color with lighter maroon veins and immature leaves which are of a light maroon color.

* * * * *

OK to print
7/26/88